US008455208B2

(12) United States Patent
Hunsucker et al.

(10) Patent No.: US 8,455,208 B2
(45) Date of Patent: Jun. 4, 2013

(54) BIOMARKERS FOR FOLLICULAR THYROID CARCINOMA AND METHODS OF USE

(75) Inventors: Stephen W. Hunsucker, Broomfield, CO (US); Bryan R. Haugen, Englewood, CO (US); Mark W. Duncan, Denver, CO (US); Romana Teodora Maier, Nijmegen (NL)

(73) Assignee: The Regents of the University of Colorado, Denver, CO (US)

( * ) Notice: Subject to any disclaimer, the term of this patent is extended or adjusted under 35 U.S.C. 154(b) by 549 days.

(21) Appl. No.: 12/596,196

(22) PCT Filed: Apr. 14, 2008

(86) PCT No.: PCT/US2008/060206
§ 371 (c)(1),
(2), (4) Date: Mar. 1, 2010

(87) PCT Pub. No.: WO2008/130887
PCT Pub. Date: Oct. 30, 2008

(65) Prior Publication Data
US 2012/0142030 A1 Jun. 7, 2012

Related U.S. Application Data

(60) Provisional application No. 60/911,875, filed on Apr. 14, 2007.

(51) Int. Cl.
*G01N 33/574* (2006.01)
(52) U.S. Cl.
USPC .............................. 435/7.23; 435/7.1; 435/7.4
(58) Field of Classification Search
None
See application file for complete search history.

(56) References Cited

U.S. PATENT DOCUMENTS

| 7,319,011 B2 | 1/2008 | Riggins et al. |
| 2006/0024692 A1* | 2/2006 | Nakamura et al. ................. 435/6 |
| 2006/0035244 A1 | 2/2006 | Riggins et al. |
| 2007/0117164 A1* | 5/2007 | Raskov et al. ............... 435/7.23 |
| 2012/0129200 A1* | 5/2012 | Ataman-Onal et al. ..... 435/7.95 |

OTHER PUBLICATIONS

Paron et al, J Mol Endocrinol, 2005, 34:199-207.*
Hooft et al, J Clin Endocrinol Metab, 2005, 90:328-334.*
Lewis M. Brown. etal.. 'Quantitiative and qualitative differences in protein expression between papillary thyroid carcinoma and normal thyroid tissue', In: Molecular Carcinogenesis, Jun. 20, 2006, vol. 45(8), pp. 613-626—see the whole document, especially Table 1.
Janete M. Cerutti, etal., 'A preoperative diagnostic test that distinguishes benign from malignant thyroid carcinoma based on gene expression', In: The Journal of Clinical Investigation, Apr. 2004, vol. I 13(8), pp. 1234-1242—see the whole document, especially Table 1; Figure 1.
La.T.Arnaldi, etal., 'Gene expression profiles reveal that DCN, DI01, and DI02 are underexpressed in benign and malignant thyroid tumors', In: Thyroid, 2005, vol. 15(3), pp. 210-222—see the whole document, especially Figure 2; Table 3.
Romana T. Netea-Maier, etal., 'Discovery and validation of protein abundance differences between follicular thyroid neoplasms', In: Cancer Research, Mar. 1, 2008, vol. 68(5), pp. 1572-1580—see the whole document.

* cited by examiner

*Primary Examiner* — Mark Halvorson
(74) *Attorney, Agent, or Firm* — Don D. Cha; Hamilton DeSanctis & Cha, LLP

(57) ABSTRACT

The present invention provides protein biomarkers for determining whether a thyroid nodule is malignant or benign and methods for using the same.

12 Claims, 12 Drawing Sheets

Table 1A. Under Abundant Proteins in FTC

| Protein name | A | B |
|---|---|---|
| Cytokeratin 8 | P05787 | 1 |
| HSP gp96/endoplasmin | P14625 | 2 |
| 78-kDa glucose-regulated protein (BiP; ER luminal $Ca^{2+}$-binding protein grp78) | P11021 | 3 |
| Calreticulin | P27797 | 4 |
| Annexin A3 (lipocortin III) | P12429 | 5 |
| β-Actin | P60709 | 6 |
| PDI A3 | P30101 | 7 |
| PDI A3 | P30101 | 8 |
| Hexokinase-1 | P19367 | 9 |
| β-Actin | P60709 | 10 |
| PDI A3 | P30101 | 11 |
| Cathepsin B | P07858 | 12 |
| HSP gp96/endoplasmin | P14625 | 13 |
| Histone H2B | P62807 | 14 |
| Glucosidase 2 β subunit | P14314 | 15 |
| Macrophage capping protein | P40121 | 16 |
| Aminoacylase-1 | Q03154 | 17 |
| Annexin A5 (lipocortin V) | P08758 | 18 |
| HSP90β | P08238 | 19 |
| Cytosolic nonspecific dipeptidase (glutamate carboxypeptidase-like protein 1) | Q96KP4 | 20 |
| Proliferation-inducing gene 4 protein (mitofilin) | Q16891 | 21 |
| ER-associated HSP40 co-chaperone (DnaJ homologue subfamily B member 11) | Q9UBS4 | 22 |
| Alcohol dehydrogenase [$NADP^+$] (aldehyde reductase) | P14550 | 23 |
| Lamin A/C | P02545 | 24 |
| TCP-1-θ (T-complex protein 1 subunit θ) | P50990 | 25 |
| p100 coactivator (staphylococcal nuclease domain-containing protein 1) | Q7KZF4 | 26 |
| 26S proteasome non-ATPase regulatory subunit 13 (26S proteasome regulatory subunit S1) | Q9UNM6 | 27 |

A = Swiss-Prot accession No.
B = Spot No. (Corresponds to the spot annotations recorded on the gel images in Fig. 3)

FIGURE 1A

Table 1B. Under Abundant Proteins in FTC

| B | C | D | E | F | G | H | I | J |
|---|---|---|---|---|---|---|---|---|
| 1 | -4.63 | -10.6 to -1.9 | 37.8 | 4.6 | -15.7 | -0.8 | 45 | 224 |
| 2 | -3.61 | -19.5 to -2.21 | 98.5 | 4.6 | 8.3 | 0 | 18 | 192 |
| 3 | -2.57 | -11.8 to -1.2 | 70.4 | 5.0 | 0 | 0 | 37 | 255 |
| 4 | -2.26 | -9.6 to -1.6 | 46.4 | 4.2 | 0 | 0 | 36 | 148 |
| 5 | -2.23 | -3.8 to -1.4 | 36.2 | 5.6 | 0 | 0 | 40 | 150 |
| 6 | -2.05 | -6.4 to 1.2 | 37.8 | 5.3 | -3.7 | 0 | 32 | 125 |
| 7 | -1.99 | -7.3 to -1.25 | 51.0 | 5.7 | -3.1 | 0.1 | 31 | 165 |
| 8 | -1.96 | -6.9 to -1.4 | 50.7 | 5.5 | -3.5 | 0 | 24 | 141 |
| 9 | -1.87 | -2.2 to -1.4 | 102.4 | 6.3 | 0 | 0 | 11 | 111 |
| 10 | -1.79 | -4.2 to 1.2 | 37.8 | 5.1 | -3.7 | -0.1 | 24 | 82 |
| 11 | -1.75 | -6.1 to -1.4 | 50.5 | 5.4 | -3.6 | -0.1 | 35 | 196 |
| 12 | -1.73 | -2.3 to -1.2 | 24.8 | 4.9 | -2.9 | -0.2 | 30 | 107 |
| 13 | -1.66 | -2.5 to –1.1 | 97.9 | 4.8 | 7.7 | 0 | 17 | 96 |
| 14 | -1.64 | -3.9 to 1.0 | 13.6 | 10.3 | 0 | 0 | 52 | 85 |
| 15 | -1.63 | -2.5 to 1.0 | 88.9 | 4.3 | 31.0 | 0 | 19 | 130 |
| 16 | -1.59 | -2.8 to 1.0 | 37.8 | 6.0 | -0.6 | 0.1 | 21 | 76 |
| 17 | -1.57 | -1.9 to -1.4 | 38.2 | 5.9 | -7.6 | 0.1 | 31 | 181 |
| 18 | -1.57 | -2.1 to 1.0 | 34.0 | 4.7 | -1.7 | -0.1 | 20 | 101 |
| 19 | -1.5 | -1.6 to -1.3 | 91.2 | 4.8 | 8.0 | -0.1 | 29 | 132 |
| 20 | -1.49 | -1.6 to -1.1 | 45.6 | 5.7 | -7.1 | 0.1 | 33 | 181 |
| 21 | -1.43 | -1.8 to 1.0 | 83.6 | 6.0 | 0 | 0 | 45 | 282 |
| 22 | -1.43 | -2.4 to 1.0 | 37.8 | 6.2 | -0.2 | 0.4 | 35 | 168 |
| 23 | -1.38 | 1.9 to -1.1 | 37.8 | 6.9 | 1.4 | 0.6 | 45 | 176 |
| 24 | -1.33 | -1.7 to -1.1 | 74.1 | 6.5 | 0 | 0 | 41 | 215 |
| 25 | -1.3 | -1.7 to 1.0 | 54.0 | 5.3 | -5.3 | 0 | 30 | 153 |
| 26 | -1.28 | -1.6 to -1.1 | 102.8 | 7.3 | 0.8 | 0.5 | 13 | 127 |
| 27 | -1.28 | 1.5–1.0 | 37.8 | 5.6 | -5.0 | 0.1 | 17 | 72 |

B = Spot No. (Corresponds to the spot annotations recorded on the gel images in Fig. 3)
C = Average intensity ratio
D = Range of intensity ratios
E = Measured MW (kDa)
F = Measured pI
G = ΔMW from predicted (kDa), i.e., differences between measured and calculated values
H = ΔpI from predicted, i.e., differences between measured and calculated values
I = % Coverage
J = Mascot score

FIGURE 1B

Table 2A. Over Abundant Proteins in FTC

| Protein name | A | B |
|---|---|---|
| 14-3-3 protein γ | P61981 | 28 |
| Tubulin β-1 chain (β-tubulin isotype I) | P69893 | 29 |
| β-Actin | P60709 | 30 |
| Peptidyl-prolyl *cis-trans* isomerase A (rotamase A) | P62937 | 31 |
| Pyridoxine-5-phosphate oxidase | Q9NVS9 | 32 |
| β-Actin | P60709 | 33 |
| Actin-related protein 2/3 complex subunit 2 | O15144 | 34 |
| Peroxiredoxin-2 (thioredoxin peroxidase 1) | P32119 | 35 |
| Nucleoside-diphosphate kinase 1 isoform b | P15531 | 36 |
| Dodecenoyl-CoA isomerase (3,2-*trans*-enoyl-CoA isomerase) | P42126 | 37 |
| Dihydrolipoamide succinyltransferase component of 2-oxoglutarate dehydrogenase complex | P36957 | 38 |
| Cytokeratin 18 (424 AA)* | P05783 | 39 |
| Cytokeratin 8 | P05787 | 40 |
| Cytokeratin 8 | P05787 | 41 |
| Histone H2B | P62807 | 42 |
| Cytokeratin 7 | P08729 | 43 |

A = Swiss-Prot accession No.
B = Spot No. (Corresponds to the spot annotations recorded on the gel images in Fig. 3)
* Comparisons of experimental and theoretical MW and pI and MS sequence coverage suggest that this is a fragment of cytokeratin 18.

FIGURE 2A

Table 2B. Over Abundant Proteins in FTC

| B | C | D | E | F | G | H | I | J |
|---|---|---|---|---|---|---|---|---|
| 28 | 1.2 | 1.0–1.4 | 28.2 | 4.5 | 0 | -0.2 | 36 | 130 |
| 29 | 1.21 | 1.0–1.3 | 40.2 | 6.5 | -9.3 | 1.7 | 19 | 65 |
| 30 | 1.21 | 1.0–1.4 | 37.8 | 5.0 | -3.7 | -0.2 | 32 | 174 |
| 31 | 1.21 | 1.1–1.4 | 16.9 | 8.1 | -0.9 | 0.2 | 35 | 86 |
| 32 | 1.25 | 1.0–1.4 | 26.6 | 6.2 | -3.3 | -0.3 | 30 | 84 |
| 33 | 1.32 | 1.0–1.5 | 37.9 | 5.1 | -3.6 | -0.1 | 34 | 164 |
| 34 | 1.36 | 1.0–1.8 | 33.5 | 7.0 | -0.8 | 0.2 | 21 | 80 |
| 35 | 1.51 | 1.1–2.2 | 22.5 | 5.0 | 0.7 | -0.5 | 34 | 85 |
| 36 | 1.56 | 1.0–2.9 | 17.1 | 5.8 | 0 | 0 | 53 | 84 |
| 37 | 1.57 | 1.0–2.8 | 28.6 | 5.8 | -0.1 | -0.1 | 16 | 75 |
| 38 | 1.7 | 1.0–2.3 | 46.3 | 5.8 | 4.9 | 0 | 23 | 102 |
| 39 | 1.85 | 1.4–2.3 | 38.6 | 5.2 | -9.2 | 0 | 36 | 264 |
| 40 | 1.93 | 1.0–2.7 | 44.8 | 5.5 | -8.7 | 0 | 35 | 251 |
| 41 | 2.32 | 1.6–2.9 | 44.8 | 5.4 | -8.7 | -0.1 | 35 | 192 |
| 42 | 2.5 | 1.3–4.6 | <13.0 | 4.8 | ND | -5.4 | 56 | 106 |
| 43 | 2.62 | 1.3–4.4 | 44.4 | 5.3 | -6.8 | -0.1 | 34 | 190 |

ND = not determined
B = Spot No. (Corresponds to the spot annotations recorded on the gel images in Fig. 3)
C = Average intensity ratio
D = Range of intensity ratios
E = Measured MW (kDa)
F = Measured pI
G = ΔMW from predicted (kDa), i.e., differences between measured and calculated values
H = ΔpI from predicted, i.e., differences between measured and calculated values
I = % Coverage
J = Mascot score

FIGURE 2B

Table 3A. Results of HSP gp96, PDI A3, and calreticulin staining in 18 patients with FTA

| Sample no. | Size (cm) | Capsular invasion | Vascular invasion | HSP gp96* | PDI A3* | Calreticulin* |
|---|---|---|---|---|---|---|
| FTA | | | | | | |
| 1 | 1 | - | - | 3 | 4 | 4 |
| 2 | 1.5 | - | - | 4 | 3 | 3 |
| 3 | 3.5 | - | - | 3 | 3 | 4 |
| 4 | 3.5 | - | - | 3 | 3 | 4 |
| 5 | 2.2 | - | - | 3 | 3 | 4 |
| 6 | 2 | - | - | 3 | 4 | 3 |
| 7 | 2 | - | - | 3 | 3 | 3 |
| 8 | 2.4 | - | - | 3 | 4 | 3 |
| 9 | 2 | - | - | 2 | 3 | 4 |
| 10 | 3 | - | - | 4 | 3 | 3 |
| 11 | 4 | - | - | 3 | 3 | 3 |
| 12 | NA | - | - | 4 | 3 | 3 |
| 13 | 5 | - | - | 3 | 4 | 4 |
| 14 | 3 | - | - | 3 | 3 | 4 |
| 15 | 1.2 | - | - | 4 | 3 | 4 |
| 16 | 0.8 | - | - | 3 | 3 | 3 |
| 17 | 2.8 | - | - | 2 | 3 | 3 |
| 18 | 3 | - | - | 2 | 4 | 3 |
| Mean score (SD) | | | | 3.1 (0.6) | 3.3 (0.5) | 3.4 (0.5) |

\* = Intensity scores: 0 to 4 (0, no staining; 4 intense staining)
NA = Not available
SD = Standard deviation

FIGURE 6A

Table 3B. Results of HSP gp96, PDI A3, and calreticulin staining in 16 patients with FTC.

| Sample no. | Size (cm) | Capsular invasion | Vascular invasion | HSP gp96* | PDI A3* | Calreticulin* |
|---|---|---|---|---|---|---|
| FTC | | | | | | |
| Minimally invasive | | | | | | |
| 1 | 4 | + | - | 4 | 3 | 3 |
| 2 | 2.6 | + | - | 3 | 3 | 3 |
| 3 | 3 | + | - | 2 | 2 | 3 |
| 4 | 2.5 | + | + | 3 | 3 | 3 |
| 5 | 3.3 | + | + | 3 | 3 | 4 |
| 6 | 5 | + | + | 2 | 3 | 3 |
| 7 | 3.5 | + | + | 2 | 3 | 3 |
| 8 | NA | + | + | 3 | 4 | 3 |
| 9 | NA | + | + | 4 | 2 | 2 |
| 10 | 3.5 | + | + | 3 | 3 | 3 |
| 11 | 2.5 | + | + | 2 | 2 | 3 |
| Mean score (SD) | | | | $2.8 (0.8)^1$ | $2.8 (0.6)^2$ | $3.0 (0.4)^2$ |
| Widely invasive | | | | | | |
| 1 | 3 | + | + | 2 | 2 | 2 |
| 2 | 3 | + | + | 3 | 3 | 3 |
| 3 | NA | + | + | 2 | 3 | 2 |
| 4 | NA | + | + | 2 | 2 | 3 |
| 5 | 5.5 | + | + | 2 | 2 | 2 |
| Mean score (SD) | | | | 2.2 (0.4) | 2.4 (0.5) | $2.4 (0.5)^3$ |
| All FTC | | | | | | |
| Mean score (SD) | | | | $2.6 (0.7)^4$ | $2.7 (0.6)^5$ | $2.8 (0.4)^5$ |

\* = Intensity scores: 0 to 4 (0, no staining; 4 intense staining)
NA = Not available
SD = Standard deviation
1 = P = 0.37 for the difference between mean minimally invasive FTC and FTA scores.
2 = P < 0.05 for the difference between mean minimally invasive FTC and FTA scores.
3 = P < 0.05 for the difference between mean minimally and widely invasive FTC scores.
4 = P = 0.07 for the difference between mean FTC and FTA scores.
5 = P < 0.002 for the difference between mean FTC and FTA scores.

FIGURE 6B

Table 4. Sensitivity analysis of immunohistochemical staining

| Marker | Sensitivity (%) | Specificity | PPV (%) | NPV (%) | Widely invasive FTC (% positive) |
|---|---|---|---|---|---|
| ≤2+ (positive) | | | | | |
| HSP gp96 | 50 | 83 | 72 | 65 | 80 |
| PDI A3 | 37 | 100 | 100 | 64 | 60 |
| Calreticulin | 25 | 100 | 100 | 60 | 60 |
| Any ≤2 | 56 | 75 | 75 | 68 | 80 |
| All ≤2 | 12 | 100 | 100 | 56 | 40 |
| PDI A3/calreticulin ≤2 | 18 | 100 | 100 | 58 | 40 |
| ≤3+ (positive) | | | | | |
| HSP gp96 | 87 | 22 | 50 | 66 | 100 |
| PDI A3 | 93 | 27 | 53 | 83 | 100 |
| Calreticulin | 93 | 44 | 60 | 88 | 100 |
| All ≤3 | 75 | 77 | 75 | 77 | 100 |
| PDI A3/calreticulin ≤3 | 87 | 61 | 66 | 84 | 100 |

PPV = Positive predictive value
NPV = Negative predictive value

FIGURE 7

BIOMARKERS FOR FOLLICULAR THYROID CARCINOMA AND METHODS OF USE

CROSS-REFERENCE TO RELATED APPLICATIONS

This application claims the priority benefit of U.S. Provisional Application No. 60/911,875, filed Apr. 14, 2007, which is incorporated herein by reference in its entirety.

FIELD OF THE INVENTION

The invention relates to methods for determining whether a thyroid nodule is malignant or benign. In particular, the invention relates to methods for analyzing a thyroid nodule comprising determining a protein level in follicular thyroid nodules.

BACKGROUND OF THE INVENTION

Thyroid cancer is one of the most common endocrine malignancies with the most common clinical presentation being a thyroid nodule. It is believed that approximately 300,000 people per year in the United States have a clinical presentation of a thyroid nodule. Currently, the fine-needle aspiration biopsy (FNAB) is used in the initial work-up of a patient with a thyroid nodule to determine whether the thyroid nodule is malignant or benign.

Distinguishing between different thyroid neoplasms of benign follicular thyroid adenoma (FTA) and malignant follicular thyroid carcinoma (FTC) based on cytological examination is particularly challenging, due to the similar cytomorphological features of these tumors and often it requires histological examination of the tissue sample. Approximately 70% of the results from FNAB are classified as benign, 5% as malignant and the remaining as either indeterminate or suspicious (25%), in which case the patient should undergo diagnostic thyroidectomy in order to exclude malignancy. Up to 80% of the indeterminate cases are diagnosed as benign follicular thyroid adenoma, indicating removal of the thyroid was unnecessary. Complications from a thyroidectomy are rare (1-3%), but the procedure is expensive and there are lifelong consequences (e.g., thyroid hormone replacement and calcium deficiency treatment).

Therefore, in order to reduce the number of unnecessary operations there is a need for a diagnostic test that is more accurate than conventional methods.

SUMMARY OF THE INVENTION

Some aspects of the invention provide a method for determining thyroid conditions. In some embodiments, methods of the invention provide a method for determining whether a thyroid nodule is malignant or benign. Some methods of the invention comprise determining the abundance of a marker protein in a sample. The sample comprises a thyroid nodule, a tissue, a fluid sample (e.g., blood), or a combination thereof. The marker protein comprises a protein of Table 1, Table 2, or a combination of two or more proteins thereof. The abundance of marker protein(s) (e.g., mass of protein per volume of serum) in a subject is then compared with the abundance of marker protein(s) in normal population (i.e., subjects without a thyroid nodule), FTA population, FTC population, or a combination of two or more thereof, to determine whether the thyroid nodule is malignant or benign.

In one embodiment, under abundance of one or more proteins of Table 1 is used as an indication that the thyroid nodule is malignant.

Yet in another embodiment, over abundance of one or more proteins of Table 2 is used as an indication that the thyroid nodule is malignant.

Still in another embodiment, a combination of under abundance of one or more proteins of Table 1 and over abundance of one or more proteins of Table 2 is used as an indication that the thyroid nodule is malignant.

In some embodiments, the method comprises determining the abundance of a plurality of proteins from Table 1, Table 2, or a combination thereof.

Other aspects of the invention provide a method for determining whether a thyroid nodule is malignant or cancerous, said method comprising determining the abundance of a marker protein of the thyroid nodule, wherein the marker protein comprises a protein listed in Table 1, Table 2, or a combination of at least two proteins.

In some embodiments, the abundance of at least two marker proteins is determined. In other embodiments, the abundance of at least three marker proteins is determined.

Yet in other embodiments, the abundance of protein is determined using an analytical method comprising enzyme-linked immunosorbent assay (ELISA), western blot, mass spectrometry, or a combination thereof.

Still other aspects of the invention provide a method for diagnosing whether a subject having a thyroid nodule has follicular thyroid carcinoma, said method comprising determining the abundance of a marker protein from the subject's sample, wherein the subject's sample comprises subject's thyroid nodule, tissue, fluid sample, or a combination thereof, and wherein the marker protein comprises a protein listed in Table 1, Table 2, or a combination of two or more proteins thereof. The under abundance of a protein in Table 1 or over abundance of a protein of Table 2 is an indication that the subject has follicular thyroid carcinoma.

In some embodiments, the abundance of at least 2 proteins in Table 1 is determined.

Yet in other embodiments, the abundance of at least 2 proteins of Table 2 is determined.

Still in other embodiments, the abundance of one or more proteins in Table 1 and the abundance of one or more proteins in Table 2 is determined.

Still in other embodiments, the marker protein comprises hexokinase-1, glucosidase 2 beta subunit, aminoacylase-1, HSP 90-beta, cytosolic nonspecific dipeptidase (glutamate carboxypeptidase-like protein 1), p100 co-activator (Staphylococcal nuclease domain-containing protein 1), 26S proteasome non-ATPase regulatory subunit 13 (26S proteasome regulatory subunit S1), 14-3-3 protein gamma, pyridoxine-5'-phosphate oxidase, nucleoside-diphosphate kinase 1 isoform b, dodecenoyl-CoA isomerase (3,2-trans-enoyl-CoA isomerase), or a combination thereof. In some embodiments, the marker protein comprises at least one of the marker proteins described above along with any other marker proteins listed in Tables 1 and/or 2.

In other embodiments, the marker protein comprises collagen alpha-2(VI) chain, annexin A5 (lipocortin V), proliferation-inducing gene 4 protein (mitofilin; mitochondrial inner membrane protein), ER-associated Hsp40 co-chaperone (DnaJ homolog subfamily B member 11), lamin-A/C, TCP-1-theta (T-complex protein 1 subunit theta), tubulin beta-1 chain (beta-tubulin isotype I) (class I beta tubulin), actin-related protein 2/3 complex subunit 2, or a combination thereof.

Yet other aspects of the invention provide a method for analyzing the thyroid condition in a subject, said method comprising determining the abundance of a marker protein, wherein the marker protein comprises a protein of Table 1, Table 2, or a combination of two or more proteins thereof. The under abundance of the protein of Table 1, over abundance of the protein of Table 2, or a combination thereof is an indication that the thyroid nodule is cancerous.

In some embodiments the method comprises determining the abundance of the marker protein from a thyroid nodule, blood sample, fine needle aspiration biopsy, or a combination thereof.

Still other aspects of the invention provide a method for determining response to thyroid cancer therapy comprising determining the abundance of a marker protein, wherein the marker protein comprises a protein of Table 1, Table 2, or a combination of two or more proteins thereof. Over abundance of one or more proteins of Table 1, under abundance of one or more proteins of Table 2, or a combination thereof, relative to the protein abundance prior to the thyroid cancer therapy is an indication that the thyroid cancer therapy is effective.

Still other aspects of the invention provide a method for determining whether a thyroid nodule in a subject is a follicular thyroid adenoma (FTA) or a follicular thyroid carcinoma (FTC). The method generally comprises determining the abundance of a marker protein in a sample obtained from the subject, wherein the sample comprises a thyroid nodule, a tissue, a fluid sample, or a combination thereof, and wherein the marker protein comprises a protein of Table 1A, Table 2A, or a combination thereof, and wherein under abundance of the protein of Table 1A, over abundance of the protein of Table 2A, or a combination thereof is an indication that the thyroid nodule is malignant. In some embodiments, the method comprises determining abundance of a plurality of proteins from Table 1A, Table 2A or a combination thereof. In other embodiments, the marker protein comprises HSP gp96, PDI A3, calreticulin, or a combination thereof.

Still in other embodiments, the marker protein comprises at least two proteins. Yet in other embodiments, the marker protein comprises at least three proteins.

In other embodiments, the step of determining the abundance of a marker protein comprises comparing the protein level to a reference protein level. Within these embodiments, in some cases, the reference protein level comprises a protein level in a subject having follicular thyroid adenoma (FTA). In other cases, the reference protein level comprises a protein level in a subject having a follicular thyroid carcinoma (FTC).

Yet other aspects of the invention provide a method for determining whether a follicular-derived thyroid neoplasm in a subject is malignant or benign. The method typically comprises determining a level of a marker protein in a sample obtained from the subject, wherein the sample comprises a thyroid nodule, a tissue, a fluid sample, or a combination thereof, and wherein the marker protein comprises a protein listed in Table 1A, Table 2A, or a combination thereof, and determining whether the follicular-derived thyroid neoplasm in the subject is malignant or benign using the determined marker protein level.

In some embodiments, the step of determining whether the follicular-derived thyroid neoplasm in the subject is malignant or benign comprises comparing the determined marker protein level to a reference protein level. Within these embodiments, in some cases the reference protein level comprises a protein level in a subject having follicular thyroid adenoma (FTA). Still in other cases, the reference protein level comprises a protein level in a subject having follicular thyroid carcinoma (FTC).

In other embodiments, under abundance of the protein of Table 1, over abundance of the protein of Table 2, or a combination thereof is an indication that the follicular-derived thyroid neoplasm is follicular thyroid carcinoma (FTC).

Yet in other embodiments, the marker protein comprises at least two proteins. Still in other embodiments, the marker protein comprises at least three proteins.

Still in some embodiments, the abundance of the marker protein is determined using an analytical method comprising enzyme-linked immunosorbent assay (ELISA), immunoblot, immunohistochemistry, mass spectrometry or a combination thereof.

In other embodiments, the marker protein comprises hexokinase-1, glucosidase 2 beta subunit, aminoacylase-1, HSP 90-beta, cytosolic nonspecific dipeptidase (glutamate carboxypeptidase-like protein 1), p100 co-activator (Staphylococcal nuclease domain-containing protein 1), 26S proteasome non-ATPase regulatory subunit 13 (26S proteasome regulatory subunit S1), 14-3-3 protein gamma, pyridoxine-5'-phosphate oxidase, nucleoside-diphosphate kinase 1 isoform b, dodecenoyl-CoA isomerase (3,2-trans-enoyl-CoA isomerase), or a combination thereof. Still in other embodiments, the marker protein comprises HSP gp96, PDI A3, calreticulin, or a combination thereof.

Other aspects of the invention provide a method for determining a subject's response to a thyroid cancer therapy comprising determining the abundance of a marker protein of the subject, wherein the marker protein comprises a protein of Table 1A, Table 2A, or a combination of two or more proteins thereof, and wherein the protein abundance following therapy relative to the protein level prior to the thyroid cancer therapy is used to determine the effectiveness of the thyroid cancer therapy. In some embodiments, an increase in the abundance of a marker protein of Table 1A, decrease in the abundance of a marker protein of Table 2A, or a combination thereof following the thyroid cancer therapy is an indication that the thyroid cancer therapy is effective.

Yet other aspects of the invention provide a kit for determining whether a follicular-derived thyroid neoplasm in a subject is malignant or benign. The kit typically comprises: a protein binding molecule for binding a marker protein, wherein the marker protein comprises a protein listed in Table 1A, Table 2A, or a combination thereof; and a labeling compound that binds to a complex formed from the protein binding molecule and the marker protein thereby allowing a determination of the marker protein level.

In some embodiments, the kit further comprises a reference protein level chart. Within these embodiments, in some cases the reference protein level chart comprises the level of proteins in Table 1A, Table 2A, or a combination thereof in a subject having follicular thyroid adenoma (FTA), follicular thyroid carcinoma (FTC), or a combination thereof.

Still in other embodiments, the labeling compound comprises fluorescent moiety.

BRIEF DESCRIPTION OF THE DRAWINGS

FIG. 1A is a table comprising a list of some of the under abundant proteins in FTC relative to FTA.

FIG. 1B is a table comprising physical data of proteins in Table 1A.

FIG. 2A is a table comprising a list of some of the over abundant proteins in FTC relative to FTA.

FIG. 2B is a table comprising physical data of proteins in Table 2A.

FIG. 3A are protein spots that are under abundant in FTC. FIG. 3B are protein spots that are over abundant in FTC. The spot numbers correspond to the spot numbers listed in FIGS. 1A-2B.

FIGS. 6A and 6B are tables showing results of HSP gp96, PDI A3, and calreticulin staining in 16 patients with FTC and 18 patients with FTA. Abbreviation: NA=not available. Figure legends: *Intensity scores: 0 to 4 (0, no staining; 4, intense staining) 1. P=0.37, for the difference between mean minimally invasive FTC and FTA scores. 2. P<0.05, for the difference between mean minimally invasive FTC and FTA scores. 3. P<0.05, for the difference between mean minimally and widely invasive FTC scores. 4. P=0.07, for the difference between mean FTC and FTA scores. 5. P<0.002, for the difference between mean FTC and FTA scores.

FIG. 7 is a table showing sensitivity analysis of immunohistochemical staining Abbreviations: PPV=positive predictive value; NPV=negative predictive value.

DETAILED DESCRIPTION OF THE INVENTION

Figure 3A:
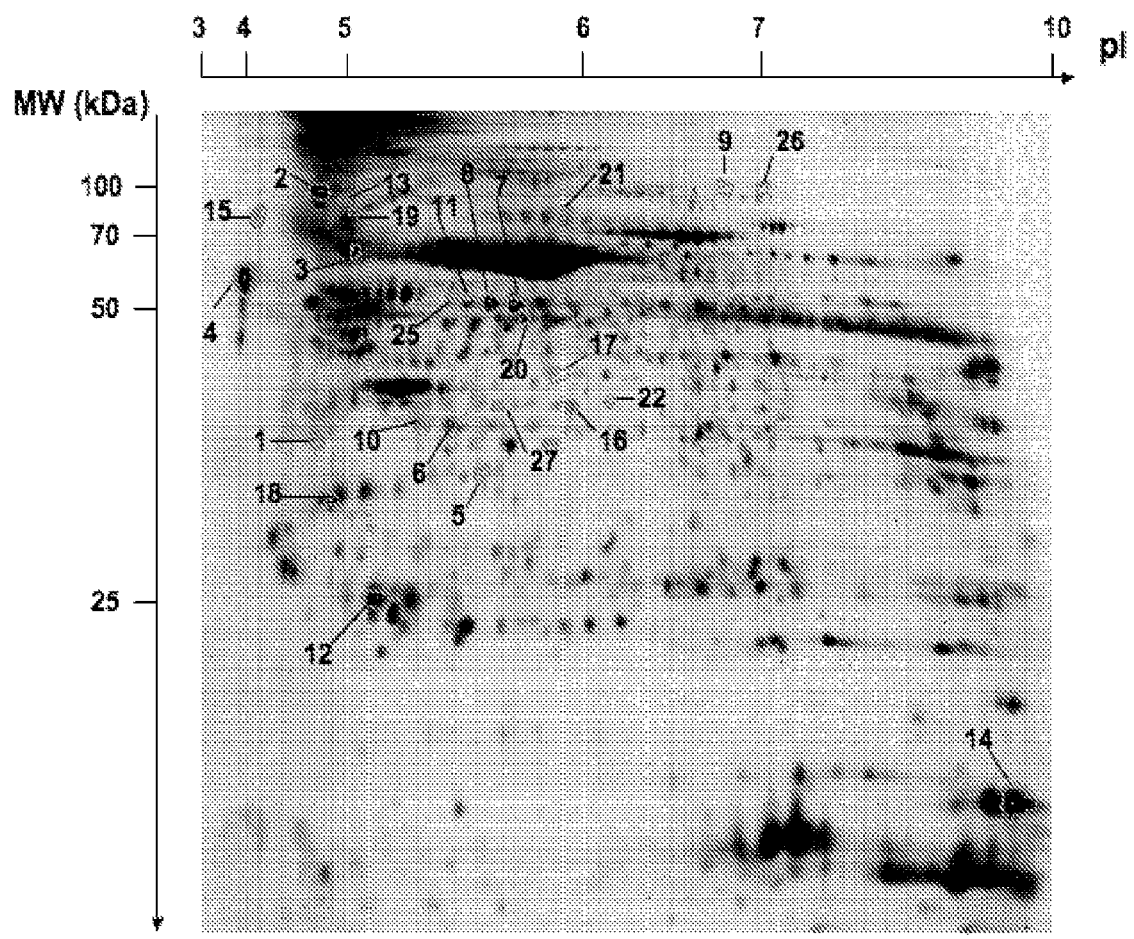
FIGS. 3A and 3B are representative two-dimensional gel images of the Cy2-labeled proteins that comprise the internal standard. The grey outlines give the position of identified protein spots that had statistically different abundance (P<0.05) between FTC and FTA.

Distinguishing between benign follicular thyroid adenoma (FTA) and malignant follicular thyroid carcinoma (FTC) by cytologic features alone is currently difficult. Molecular markers may aid distinguishing FTA from FTC in patients with indeterminate cytology.

Some aspects of the invention provide methods for determining whether a thyroid tumor or nodule in a subject is malignant (e.g., FTC) or benign (e.g., FTA). Other aspects of the invention provide methods of diagnosis, prognosis, and/or pathophysiology of follicular-derived thyroid neoplasms.

Thyroid cancer is the most common endocrine malignancy and its most frequent clinical presentation is as a thyroid nodule, either solitary or within a multinodular goiter. Approximately 5% to 10% of adults have palpable thyroid nodules and 30% to 50% have nodules identified by ultrasound. Although the majority of these are benign, approximately 5% to 7% of thyroid nodules are malignant. Fine-needle aspiration biopsy (FNAB) is the conventional diagnostic test in the initial evaluation of a patient with a thyroid nodule and offers a diagnostic accuracy of between 70% and 97% in experienced centers. Typically, about 70% of FNAB are classified as benign, 4% are classified as malignant [predominantly papillary thyroid carcinomas (PTC)], 2% to 10% supply insufficient sample, and the remainder are classified as either indeterminate or suspicious (5-23%). Typically, patients returning either indeterminate or suspicious results undergo diagnostic hemithyroidectomy or complete thyroidectomy to exclude malignancy.

It is particularly challenging to distinguish between thyroid neoplasms of the follicular type, i.e., benign follicular thyroid adenoma (FTA), malignant follicular thyroid carcinoma (FTC), and follicular variant of papillary carcinoma, based on cytologic examination alone. These tumors have similar cytologic features and surgery is usually required to obtain a definitive tissue sample. However, because only 5% to 7% of the clinically identified nodules prove to be malignant, the indeterminate findings subject most patients to unnecessary surgery, potential risks, and, occasionally, irreversible complications.

Differentiated epithelial thyroid tumors represent a spectrum of morphologically and biologically diverse neoplasms and the molecular etiology and pathogenesis of thyroid carcinoma, of the follicular type, is unknown. Thyroid cancer is believed to result from the accumulation of oncogene mutations or rearrangements (RAS, BRAF, RET, NTRK1, and MET) and silencing of tumor suppressor genes (p53, RASSF1A, PTEN, PPARc, and CDK inhibitors. Recent data suggest that the so-called atypical FTA, which is characterized by high cellular density, mitoses, and a less regular cytologic pattern, may share genetic features with both FTC and PTC, but the progression of thyroid adenoma to carcinoma has not been clearly shown. Therefore, defining the differences in protein levels that distinguish between FTA and FTC provides additional insight in the earliest steps of follicular neoplasia transformation and provide a clinical tool that could improve the diagnostic accuracy of FNAB in patients with indeterminate cytology.

Some aspects of the invention provide protein abundance differences between FTA and FTC tissue. Many cellular processes are regulated post transcriptionally and mRNA studies are not well suited for determining some differences that affect tumor biology. Consequently, proteomics provide a useful tool for understanding the disease processes. Peptides and proteins can be measured by well-established methods with high sensitivity, precision, and accuracy. In some embodiments, changes in marker protein level(s) provide a sensitive and/or specific protein based diagnostic test for follicular-derived thyroid neoplasms.

New molecular biological techniques have improved the sensitivity and specificity of detection of primary and recurrent cancer in different types of neoplasia. However, the molecular etiology and pathogenesis of epithelial thyroid carcinoma and especially the follicular-derived thyroid carcinoma are not well understood. Some data suggest that atypical FTA, which are characterized by high cellular density, mitoses and a less regular cytological pattern, might share genetic features with both follicular and papillary cell carcinomas. However, the adenoma-carcinoma sequence, which is accepted for some other cancers, has not been demonstrated for the thyroid cancers.

Some aspects of the invention provide a panel of protein biomarkers that can be quantified in tissue and/or blood samples from subjects with thyroid nodules. The abundance of these protein markers differs between populations, e.g., normal population (i.e., those without a thyroid nodule), FTC population and FTA population. In one particular embodiment, marker protein abundance (e.g., mass of protein per mass of tissue or volume of blood) is determined using methods that are well known to one skilled in the art, such as ELISA. Without being bound by any theory, it is believed that thyroid tumorigenesis is a complex process associated with quantitative and qualitative changes in proteins, e.g., abundance and post-translational modifications. Using a differential proteomics approach the present inventors have found that there are differences in protein abundances between FTC population and FTA population. Furthermore, the present inventors have identified marker proteins that can be used to differentiate between the benign and malignant forms of follicular-derived thyroid neoplasia. These differences are used, for example, as diagnostic tools as well as to provide new insight in the pathogenesis of follicular thyroid neoplasia. Accordingly, some aspects of the invention provide molecular markers, for example, marker proteins, that are used to determine whether a subject's thyroid nodule is malignant or benign. In some embodiments, methods of the invention are used to determine whether the thyroid nodule is benign follicular thyroid adenoma or malignant follicular thyroid carcinoma.

Yet other aspects of the invention provide marker proteins that can be used separately or in combination to determine benign and malignant forms of follicular-derived thyroid neoplasia. In some embodiments within these aspects of the invention, the marker proteins comprise a protein listed in Table 1A, Table 2A, or a combination thereof. In other embodiments, the marker protein comprises at least two proteins. Still in other embodiments, the marker protein comprises at least three proteins. Each of the marker proteins is independently selected from Table 1A and Table 2A. Thus, in some cases all the marker proteins are selected from Table 1A or Table 2A. In other cases, the marker proteins comprise a mixture of proteins from Table 1A and Table 2A. Accordingly, it should be appreciated that the scope of the invention is not limited to any particular table of proteins.

In another embodiments, methods of the invention include determining whether the abundance of one or more marker proteins falls within the reference range for the normal population, the FTC population, the FTA population, or a combination thereof. In some particular embodiments, methods of the invention include determining whether one or more marker proteins listed in Table 1 of a subject are in the reference range for the normal population, the FTC population, the FTA population, or a combination thereof to determine whether the follicular-derived thyroid neoplasm is malignant. In yet some other particular embodiments, methods of the invention include determining whether one or more marker proteins listed in Table 2 of a subject are in the reference range for the normal population, the FTC population, the FTA population, or a combination thereof to determine whether the follicular-derived thyroid neoplasm is malignant or benign. Still in other embodiments, methods of the invention include determining whether one or more marker proteins listed in Table 1 and Table 2 of a subject are in the reference range for the normal population, the FTC population, the FTA population, or a combination thereof to determine whether the follicular-derived thyroid neoplasm is malignant or benign.

Still in other particular embodiments, methods of the invention include determining whether one or more marker proteins listed in Table 1 are within the reference range for FTA in combination with determining whether one or more marker proteins listed in Table 2 are within the reference range for FTC. In such cases, combination of one or more marker proteins in Table 1 with one or more marker proteins in Table 2 serves as an indication that the follicular-derived thyroid neoplasm is either benign or malignant. The term "reference range for" normal, FTC, or FTA refers to the abundance of a particular protein determined for the normal population, the FTC population, or the FTA population, respectively.

It should be appreciated that the accuracy of the test, e.g., diagnosis, result is likely to increase as more marker proteins are analyzed. However, the accuracy of such test does not necessarily improve linearly or geometrically as more marker proteins are analyzed. In some embodiments, a statistical significance test (e.g., t-test) is used to determine whether a particular protein level falls within the FTC or FTA level. That is, in some instances a statistical significant test is used to determine whether a particular marker protein level is more statistically significant as being a level that falls within the FTC or the FTA level.

As shown in Tables 1 and 2, marker proteins underabundant in the FTC population (relative to the FTA population) include, but are not limited to, proteins involved in protein folding (e.g., HSP gp96, PDI A3 and A6, calreticulin, DNAJB, HSP 90-beta, BIP), proteins involved in nuclear stability, chromatin structure and gene expression (e.g., lamin A/C), and thyroglobin. The proteins overabundant in the FTC population relative to the FTA population include, but are not limited to, those involved in cell stabilization against mechanical stress (e.g., cytokeratin 7, 8 and 18, tubulin), proteins associated with tumor invasiveness and metastatic potential in other types of malignancy and kinase signaling (e.g., nucleoside diphosphate kinase 1 isoform b).

In some embodiments, a marker protein is selected from the group consisting of (from Table 1) hexokinase-1, glucosidase 2 beta subunit, aminoacylase-1, HSP 90-beta, cytosolic nonspecific dipeptidase, p100 co-activator, 26S proteasome non-ATPase regulatory subunit 13, (from Table 2) 14-3-3 protein gamma, pyridoxine-5'-phosphate oxidase, nucleoside-diphosphate kinase 1 isoform b, dodecenoyl-CoA isomerase, and a mixture thereof.

As shown in Table 1, several proteins, residents of the endoplasmic reticulum (ER), showed a lower abundance in the FTC than in FTA. They are believed to be molecular chaperones that play a role in the quality control system that regulates folding and maturation of newly synthesized proteins as well as the transport of the nascent proteins from the ER to other compartments of the secretory pathway. Among these, HSP gp96 is a constitutively expressed ER molecular chaperone belonging to the HSP90 family. HSP90 has been shown to interact with a number of signaling kinases (e.g., phosphatidylinositol 3-kinase, RAF, AKT, IKK, c-Src, ErbB2) and is believed to be associated with RET/PTC1 oncoproteins that have been identified in thyroid carcinomas.

Marker proteins can also be a molecular target for antineoplastic agents for treating thyroid carcinoma. For example, it is believed that HSP gp96, as well as BIP and PDI are involved in the maturation of thyroglobulin, possibly as a part of a macromolecular process, by assisting glycosylation and folding of thyroglobulin monomers. In addition, PDI, which catalyzes thiol-disulfide interchanges that result in rearrangements of protein-disulfide bonds may also be involved in the structural modification of thyroglubulin in acidic post-ER compartments. PDI and BIP may also act in conjunction to control the thyroglubulin multimerization. HSPs are believed to be implicated in tumor cell proliferation, differentiation, invasion, metastasis of different types of neoplasia. Accordingly, modulation of marker proteins can be an effective method of treating thyroid carcinoma.

In other aspects of the invention, the abundance of marker protein(s) can be used to determine effectiveness of FTC therapy. For example, the abundance of different HSPs has been associated with the degree of tumor cell differentiation. Accordingly, abundance of different HSPs can be used to determine response to therapy in FTC.

Calreticulin is another ER protein that has been implicated in several cellular processes including $Ca^{2+}$ storage and signaling, lectin-like chaperoning, regulation of gene expression, cell adhesion and autoimmunity. The specificity of calreticulin and its homologue calnexin for binding with monoglycosylated glycan results in the association of these chaperones with most of the glycoproteins synthesized in the ER.

In other aspects of the invention, modulation of marker protein(s) can be used as antitumor vaccines. For example, in addition to their role in the control of protein folding, HSP gp96 and calreticulin elicit roles in the initiation of both the innate and adaptive immunity. These immunological functions allow modulation of HSP gp96 as an antitumor vaccine.

Analytical Methods

Any number of analytical methods known to one skilled in the science can be used to determine the abundance of marker proteins. Some of the analytical methods that can be used to determine the abundance of marker proteins include, but are not limited to, gel electrophoresis, mass spectrometry, immunochemical methods such as immunoblot, ELISA and immunohistochemistry and a combination of two or more techniques thereof.

In one particular embodiment of the invention, DIGE is used to identify the marker proteins and/or to determine the marker protein abundance. DIGE generally involves the separation and quantitation of intact proteins. One of the advantages of the DIGE approach is that it allows identification of important isoform differences. For example, for three of the marker proteins (cytokeratin 8, beta actin and histone H2B), present inventors have identified different isoforms that were differentially expressed in opposite direction in the FTC vs FTA. Comparisons of the experimental and theoretical Mw and pI and the MS sequence coverage showed that in the case of cytokeratin 8, for example, the larger and more basic isoform showing overabundance in the FTC represented the full length protein, whereas the smaller and more acidic isoform being underexpressed in the FTC represents a fragment covering amino acid 100 to 400 of the parent protein sequence.

In addition to allowing identification of posttranslational modifications, DIGE allows two different samples to be run on a single gel thereby significantly reducing the analytical variability without influencing the biological variability, thus increasing the likelihood of obtaining statistically meaningful results.

Discovery (proteomics) and validation (immunohistochemistry) tools were used to identify and confirm novel molecular markers that distinguish between FTA and FTC tissue. These protein identifications provide insight into the pathogenesis of follicular thyroid neoplasia and a subset of these biomarkers serve as sensitive and specific markers that differentiate between benign and malignant form of follicular-derived thyroid neoplasia. In some embodiments, an analytic strategy measuring intact proteins (two-dimensional gels) was used because inter alia this allowed detection and quantification changes in specific isoforms.

Genomic research has shown several genetic alterations associated with follicular neoplasia, but these alterations have only been documented in a small subset of tumors. Further, the utility of these findings is limited because the level of mRNA expression frequently does not reflect the amount of protein in the cell, in part because gene sequences cannot predict posttranslational modifications nor reflect dynamic cellular processes. Thyroid tumorigenesis is a complex process and the additional quantitative and qualitative information intrinsic to the proteomic data is helpful in understanding this complex pathophysiologic process. Although used extensively in other forms of malignancy, the proteomic approach has had limited application in studies of thyroid cancer. The present inventors have discovered that certain proteins are under abundant and some proteins are over abundant in FTC compared with FTA. For example, proteins involved in protein synthesis and folding represent a large group of under abundant proteins in FTC compared with FTA.

The present inventors have discovered that many proteins show statistically significant differences in abundance between FTC and FTA tissue. Exemplary proteins that are under abundant in FTC tissue compared with FTA are proteins involved in protein folding (e.g., HSP gp96, PDI A3, calreticulin, HSP40, HSP90β, and BiP); proteins involved in nuclear stability, chromatin structure, and gene expression (lamin A/C); and thyroglobin. Of the proteins overabundant in FTC, some are involved in cell stabilization against mechanical stress (e.g., cytokeratins 7, 8, and 18 and tubulin), whereas others are linked to tumor invasiveness and metastatic potential in other malignancies, and kinase signaling (e.g., nucleoside diphosphate kinase 1 isoform b). The present inventors have also discovered that the amount of some proteins previously associated with follicular-derived thyroid neoplasia, including nucleoside diphosphate kinase 1 (also known as nm23-H1), the nm23 metastatic suppressor gene product were also different between FTC and FTA tissue.

In some embodiments, DIGE approach was used to run several different samples on a single gel. In many instances, such a technique led to higher quantitative and/or qualitative precision. In some cases, such a technique increased the likelihood of obtaining statistically meaningful results, even when the fold change was small.

In some embodiments, proteins were further validated, for example, by immunohistochemistry in an independent subset of paraffin-embedded tissue samples. In many instances such validation showed that DIGE approach was robust for these identified proteins. In some embodiments, several residents of the endoplasmic reticulum (ER) were present at lower levels in FTC than in FTA tissue. Without being bound by any theory, it is believed that these are molecular chaperones that play a role in the quality control system that regulates folding and maturation of newly synthesized proteins as well as the transport of the nascent proteins from the ER to other compartments of the secretory pathway. Among these, some proteins such as BiP, PDI A3, and HSP gp96, a constitutively expressed ER molecular chaperone belonging to the HSP90 family, were under abundant in the FTC samples compared to FTA samples. It is believed that these proteins are involved in the maturation of thyroglobulin, possibly as a part of a macromolecular process, and assist with glycosylation and folding of thyroglobulin monomers. Calreticulin, another ER protein identified by the present inventors, plays a key role in the synthesis of glycoproteins, including thyroperoxidase. Moreover, in addition to their role in protein folding, calreticulin and HSP gp96 is believed, in some case, to trigger an anticancer immune response and improve the efficiency of phagocytosis. The present inventors have discovered that the level of these proteins were lower in FTC compared to FTA tissue.

Some proteins showed a larger difference in volume ratios between the FTC and FTA. For example, HSP gp96, PDI A3, and calreticulin proteins were abundant in the tissue samples and showed a large difference in volume ratios between the FTC and FTA. In general, the immunohistochemistry and DIGE findings were consistent for proteins selected. In each instance, the intensity scores for immunohistochemical staining correlated with disease severity, e.g., generally FTAs showed the highest scores for HSP gp96, PDI A3, and calreticulin proteins, whereas the widely invasive FTCs showed the lowest scores for HSP gp96, PDI A3, and calreticulin proteins. Some proteins, e.g., HSP gp96, PDI A3, and calreticulin, showed a high sensitivity with respect to detection of widely invasive FTCs. An immunohistochemical staining intensity score of three or less for any of the proteins detected substantially all of the widely invasive FTCs in Tables 1A-2B.

Some aspects of the invention provide methods for using proteomics and/or a validation approach (e.g., immunohistochemistry) to identify potential novel biomarkers that aid in distinguishing between malignant and benign tumor, e.g., FTC and FTA. In some embodiments, such methods also provide insights into the global pathophysiologic changes in tumor, e.g., thyroid carcinoma. Methods of the invention allow identification of protein isoform differences and post-translational modifications that may be missed by genomic or other proteomic approaches.

Additional objects, advantages, and novel features of this invention will become apparent to those skilled in the art upon examination of the following examples thereof, which are not intended to be limiting.

EXAMPLES

Tissue Samples for DIGE Analysis

Snap-frozen tumor tissue samples from 11 patients undergoing surgery for follicular neoplasms were obtained through the Cooperative Human Tissue Network. At final histopathologic diagnosis, five were identified as FTC (three women, ages 31-75 years, tumor sizes of 3.5-8 cm) and six were FTA (all women, ages 29-58 years, tumor sizes of 1.3-5.5 cm). In all FTC patients, tumor capsular invasion was present, and in two of these, the capsular invasion was extensive. In three FTC patients, vascular invasion was present, and in one of these, the vascular invasion was extensive.

Preparation of Tissue Protein Extracts

Protein was extracted from each fresh-frozen tissue sample (~50 mg). Briefly, each fresh frozen tissue sample (50 mg) was homogenized in 150 mM NaCl with 50 mM Tris (pH 7.5) with 0.3% SDS and protease inhibitors (Complete™ protease inhibitor cocktail from Roche 2× recommended concentration). The extracts were treated with 200 U/ml DNAse 1 and 20 U/ml RNAse A (Sigma). Proteins were precipitated with methanol/chloroform (Wessel et al., *Anal. Biochem.*, 1984, 138, 141-3), dried in a SpeedVac, and then rehydrated overnight in 400 µL of reaction buffer [7 mol/L urea, 2 mol/L thiourea, 4% (w/v) CHAPS]. Each sample was then supplemented with 10 mmol/L DTT (20 µL of 200 mmol/L DTT in reaction buffer), homogenized with a small pellet pestle (Kimble Kontes), and incubated for 2 h. Samples were thoroughly mixed and centrifuged (16,000×g, 15 min, room temperature), and the solubilized protein supernatants were collected. An aliquot was diluted 50-fold with water immediately before protein assay by the method described in *Anal. Biochem.*, 1976, 72, 248-54. Based on these findings, each sample was diluted to 5 mg/mL protein with reaction buffer containing 10 mmol/L DTT. Samples were flash frozen with liquid $N_2$ and stored at −80° C. until analysis.

DIGE Experiment

Each analytic DIGE gel was composed of the following: 50 µg of total protein isolated from an individual FTC sample (e.g., labeled with Cy5), 50 µg of total protein from a pool prepared from all FTA samples (e.g., labeled with Cy3), and 50 µg of total protein from a pooled internal standard. The FTA pool was created by combining equal amounts of total protein isolated from individual FTA tissue samples. There were a limited number of well-defined (histopathologically) snap-frozen FTA samples with some yielding limited amounts of total protein. Therefore, it was decided to pool protein from these tissues and compare the pool against individual FTC samples (a more heterogeneous group) rather than omit one FTA sample and randomly compare one FTA sample with one FTC sample. The internal standard, composed of an equal amount of total protein isolated from all tissue samples (five FTC plus six FTA), was always labeled with Cy2 and included on every gel to improve quantitative precision and enhance spot matching. The labeling of FTC and FTA samples was reversed on alternate gels to minimize any dye bias.

Differentially abundant proteins were identified from preparative gels containing 50 µg of the pooled internal standard labeled with Cy2 and 950 µg of unlabeled pooled internal standard. The inclusion of the Cy2-labeled proteins was to facilitate spot matching between analytic and preparative gels. Labeled and unlabeled proteins can have slightly different migration behavior resulting from dye conjugation, and therefore, gels were also post stained with Deep Purple (GE Healthcare) to visualize the corresponding unlabeled protein spots. This method allowed correct matching of the unlabeled and labeled proteins and allowed selection of correctly matched desired protein spot.

Labeling reactions were carried out as previously described. See, for example, *Electrophoresis*, 1997, 18, 2071-7 and *Mol. Carcinog.*, 2006, 45, 613-26. After labeling, the samples were combined (e.g., one sample labeled with Cy5, one sample labeled with Cy3, and the internal standard labeled with Cy2) and the mixture was taken to a final volume of 450 µL with reaction buffer, hydroxyethyl disulfide (0.1 mol/L, 5.4 µL, Destreak, GE Healthcare), 1% broad range Pharmalytes 3-10 NL (GE Healthcare), and bromphenol blue (0.003%).

After resuspension in the rehydration buffer, protein samples were passively rehydrated into 24-cm immobilized pH gradient strips (IPG 3-10 NL, GE Healthcare) for 24 h and then focused (IPGphor System, GE Healthcare) for 66,000 Vh (analytic gels) or 133,000 Vh (preparative gels). Cysteine side chains were reduced and alkylated by incubating the focused strips (10 min, room temperature) in equilibration solution [6 mol/L urea, 100 mmol/L Tris (pH 8.8), 30% glycerol, 2% SDS, 0.25% saturated aqueous bromphenol blue] containing 0.5% DTT followed by incubation in equilibration solution with 4.5% iodoacetamide (10 min, room temperature).

Gel electrophoresis was performed on precast 8% to 16% acrylamide gradient gels (Jule, Inc.) as described in *Mol. Carcinog.*, 2006, 45, 613-26. Voltage and current were continuously monitored throughout all runs for quality control.

Gels were scanned on a Typhoon 9400 Variable Mode Laser Imager (GE Healthcare) at 100 µm resolution. Laser and filter settings for each of the dyes were as follows: Cy3 (excitation, 532 nm; emission, 580 nm; bandpass, 30 nm), Cy5 (excitation, 633 nm; emission, 670 nm; bandpass, 30 nm), Cy2 (excitation, 468 nm; emission, 520 nm; bandpass, 40 nm), and Deep Purple (excitation, 532 nm; emission, 610 nm; bandpass, 30 nm).

DeCyder software (version 5.0; GE Healthcare) was used for spot detection and relative quantification of protein spots on the fluorescence images. For each gel image, the DeCyder Differential In-gel Analysis software module was initially adjusted to detect an estimated number of 2,500 spots. Individual spots at the extreme edges of the gel, extremely low intensity spots, and dust particles (i.e., those spots with a high slope) were excluded. Volumes were measured for each protein spot in the three fluorescent channels (i.e., Cy3, Cy5, and Cy2). Individual DIGE gels were matched using the Biological Variation Analysis (BVA) software module (GE Healthcare). Spots matched on at least four of the five individual gels were subjected to statistical analysis in BVA. Spot volumes of the Cy2 internal standard were used to calculate standardized volume ratios for the Cy5- and Cy3-labeled FTC and FTA protein spots. A Student's t test was used to compare the differences in protein spot volumes between the FTC and the pooled FTA samples in the individual gel analysis. Statistical significance was defined as P<0.05 (two sided).

Spots that showed a statistically significant difference in abundance between FTC and FTA were used to generate a list of candidate spots for identification. These spots were matched on the preparative gel, excised, and subjected to in-gel enzymatic digestion and identification by MALDI-TOF MS. Additional protein spots were also processed to serve as internal molecular weight (MW) and isoelectric point (pI) markers. The positions of these markers were used to generate calibration curves for protein MW (cubic spline) and pI (log linear) and to determine the observed pI and MW for each protein spot. The measured MW and pI reported in FIGS. 1A-2B (Tables 1A to 2B) have an approximate error of ±20% of the predicted values and deviations larger than this are likely the result of posttranslational modification. Predicted protein MW and pI were derived from the Swiss-Prot database using the mature protein form (chain) when available.

Protein Identification by Mass Spectrometry

Protein spot excision and in-gel enzymatic digestion were performed automatically by the Ettan Spot Picker and Ettan Spot Digester (GE Healthcare) as previously described in *Mol. Carcinog.*, 2006, 45, 613-26. All digests were analyzed by MALDI-TOF MS (Voyager DEPRO, Applied Biosystems), again as described in *J. Proteome Res.*, 2003, 2, 199-205. Spectra were collected over the range m/z 500 to 5,000. Peptide mass fingerprints were internally calibrated to monoisotopic trypsin peaks (i.e., m/z 515.33, 842.51, 1,045.56, and 2,211.10). Spectra were processed using ProTS Data (Efeckta Technologies) to generate a peak list that was then submitted to Mascot (Matrix Science Ltd.) for database searching. Spectral preprocessing included defining the baseline, noise, and signal-to-noise ratio as well as monoisotopic peak selection. A signal-to-noise ratio in ProTS Data of >4 was required for inclusion in the peak list. Database searches were conducted using the mammalian subset of the nonredundant protein database (National Center for Biotechnology Information, database release May 7, 2006 with 446,224 mammalian sequences) and the Swiss-Prot database (release 49.6 with 193,477 mammalian sequences). Other settings in ProTS included the following: peak amplitude, 100; peak width, 250; and chemical noise factor, 1.5. Settings in Mascot were as follows: peptide mass tolerance of ±100 ppm, fixed modification of carbamidomethylation of cysteine side chains, and trypsin selected as the enzyme with one missed cleavage accepted. Searches were not constrained by pI or MW. Minimum requirements for positive protein identification were described previously (*J. Proteome Res.*, 2003, 2, 199-205) and peptide and protein assignments were made according to that described in *Mol. Cell. Proteomics*, 2004, 3, 531-3.

Immunohistochemistry

Archival tissue blocks were selected from 16 patients with FTC (5 widely invasive) and 18 patients with FTA who underwent thyroid surgery at the Radboud University Nijmegen Medical Centre (Nijmegen, the Netherlands). Of the patients with FTC, preoperative FNAB was inconclusive in 10 patients (follicular cell proliferation) and suspect for carcinoma in 4 patients. In the remaining 2 patients, the FTC was found incidentally after the patients had their goiter removed because of mechanical complaints. Four-micrometer-thick sections of the paraffin-embedded tissue samples were deparaffinized in xylene and rehydrated. Antigen retrieval was performed in 20 mmol/L citrate buffer (pH 6.0) following heating in a household microwave oven (10 min at 95° C. followed by cooling down to room temperature) and brief washing in PBS. Endogenous peroxidase blocking was performed in the PT Module (Lab Vision) using $H_2O_2$ in methanol for 10 min and rinsing the slides thrice in PBS (pH 7.4). Immunohistochemistry was performed on an Autostainer (Lab Vision). Following incubation with the primary antibody [protein disulfide isomerase A3 (PDI A3) monoclonal antibody (clone RL 77), Abcam; calreticulin monoclonal antibody (clone FMC75), Abcam; heat shock protein (HSP) gp96 polyclonal antibody (clone ZMD 287), Zymed Laboratories, Invitrogen Immunodetection] for 60 min at a dilution of 1:1600 (PDI A3), 1:400 (calreticulin), and 1:200 (anti-HSP gp96), slides were reacted with an immunoperoxidase detection system (poly-HRP-ant Ms/Rb/Ra IgG, Immunologic). The slides were then rinsed in PBS (pH 7.4) thrice and localization of the staining was performed for 5 min with 3,3'-diaminobenzidine tetrahydrochloride (DAB+, Power DAB, Immunologic). After rinsing in PBS, the slides were finally counterstained with Mayer's hematoxylin, dehydrated in ethanol and xylene, and coverslipped using a nonaqueous mounting medium. Cytoplasmatic and nuclear staining was considered as a positive reaction and intensity of staining was measured. A pathologist was blinded to the histologic diagnosis and reported the results in a semiquantitative fashion: that is, no staining (0), faint (+1), low (+2), moderate (+3), and intense (+4) staining Quantification of Protein Biomarkers In this example, clinical utility of marker proteins (i.e., biomarkers) are evaluated in serum and tissue through quantitative enzyme-linked immunosorbent assays (ELISAs). ELISAs are used because they are an accepted analytical platform in clinical chemistry, provide quantification, exhibit good sensitivity, have reasonable costs and are high throughput. Serum is used in assays, but tissue can also be used in diagnostic assays. In one study, the population distribution is as follows: about 80 percent Caucasian, 10 percent Hispanic, 5 percent black and a few percent Asian and native American for both FTA and FTC. FTA 70 female, 30 male. FTC 60 female and 40 male.

Quantitative immunoaffinity-based assays are developed for the detection of each biomarker in serum and tissue from patients with thyroid nodules. Tissue samples include follicular thyroid carcinoma, follicular thyroid adenoma and matched normal tissue from an unaffected area of the same thyroid resections.

The sensitivity and specificity of each protein biomarker is defined, individually and in combination. Biomarkers are assessed for their ability to differentially diagnose follicular thyroid carcinoma and follicular thyroid adenoma. A clinically useful assay(s) is generated that allows differential diagnosis of follicular thyroid carcinoma and follicular thyroid adenoma, using large-scale, multi-center validation studies.

Assays for each biomarker are developed in rank order. There are often multiple isoforms of the protein of interest and assays that target one specific form is developed to provide the diagnostic specificity and sensitivity. Commercially available antibodies and pure protein standards are used to develop ELISAs for quantification of biomarkers in serum and tissue.

Each biomarker is validated in a population of patients with known, well defined clinical outcomes. Tissue and blood samples from the thyroid tissue bank that include matched normal tissue from an unaffected area of the thyroid are used. About 100-200 tissue and blood samples are collected per year. Tissue is homogenized and proteins extracted prior to quantification of biomarkers by ELISA. Biomarker quantities are measured directly from serum by ELISA. Multiplexed ELISAs are developed for panels of biomarkers.

Logistic regression and multiple logistic regression are used to assess the biomarkers individually and in combination for their diagnostic value in discriminating between FTC and FTA. Receiver Operating Characteristic (ROC) curves from the non-linear regression models quantifies the sensitivity and specificity of the individual biomarkers and combinations of biomarkers.

Statistical Considerations

The sensitivity and specificity of each protein biomarker is defined individually and in combination. The sensitivity and specificity of each biomarker, individually and in combination, are assessed for diagnostic power. Logistic regression and multiple logistic regression are used to assess the biomarkers individually and in combination for their predictive value in discriminating between healthy subjects, subjects with follicular thyroid adenoma and subjects with follicular thyroid carcinoma. Receiver Operating Characteristic (ROC) curves from the non-linear regression models are used to quantify the sensitivity and specificity of the individual biomarkers and combinations of biomarkers. In some embodiments, logistic mixed modeling is also utilized.

Power analysis is used to determine the sample size needed to make statistical judgments that are accurate and reliable. The power analysis is undertaken for each biomarker given the characteristics of each distinct analyte and assay. The effectiveness of each biomarker in distinguishing between low- and high-risk populations is examined using the receiver operating characteristic (ROC) curve. Statistical analyses are based on false and true positive rates, and to avoid bias, only samples from patients with an unambiguous diagnosis are used.

DIGE Image Analysis and Protein Identification

Figure 3B:
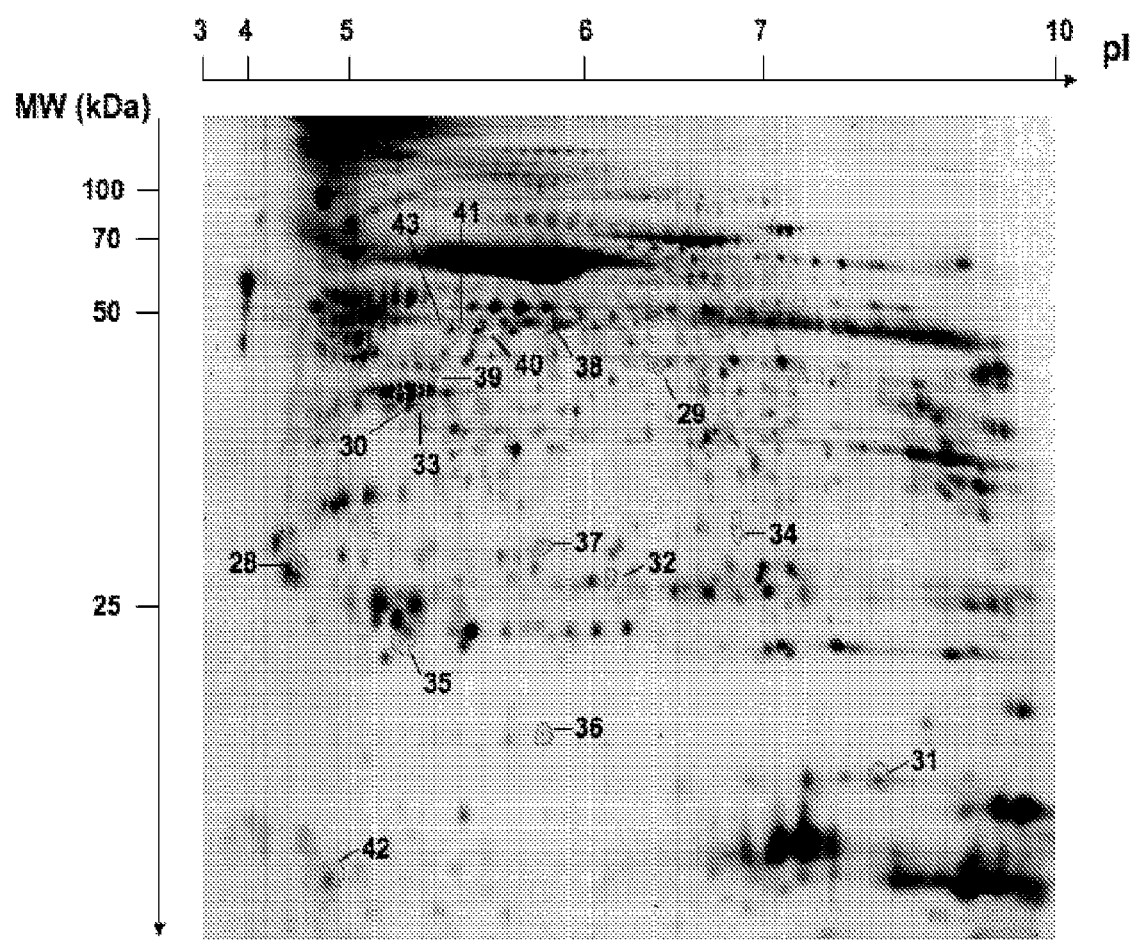
Figure 4A:
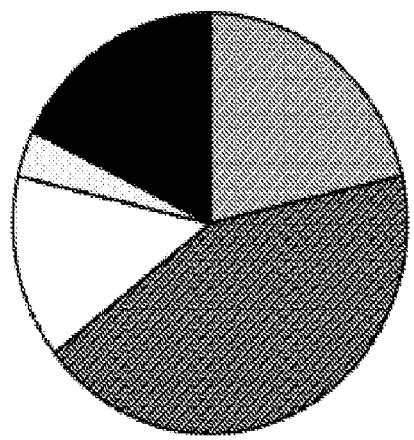
FIG. 4A shows distribution of some of the identified proteins that are under abundant in FTC relative to FTA according to their cellular function.
Figure 4B:
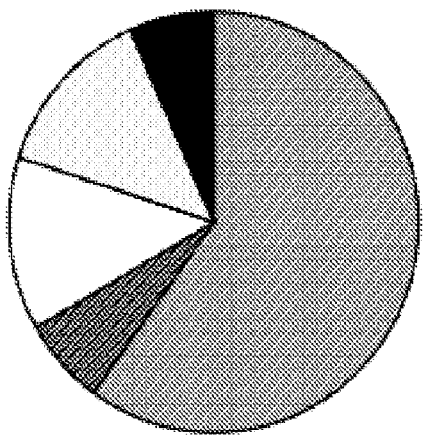
FIG. 4B shows distribution of some of the identified proteins that are over abundant in FTC relative to FTA according to their cellular function.

More than 1,500 protein spots were detected on each analytic DIGE gel and a total of 680 of these were matched on four of five individual gels and the pooled sample gel. Fifty-four of the protein spots that showed statistically significant ($P<0.05$) abundance differences between individual FTC samples and the FTA pool were identified (FIGS. 3A and 3B). Eleven proteins were excluded from further analysis: that is, albumin, β-globin, thyroglobulin (four distinct spots), and five spots that were identified as a mixture of several proteins. This left 43 protein spots for further consideration (Tables 1A-2B in FIGS. 1A-2B). Of these, 27 spots, corresponding to 23 distinct protein entities, were less abundant (average fold changes, 1.28-4.63) in FTC versus FTA; 16 spots, corresponding to 14 distinct proteins entities, were more abundant (average fold changes, 1.20-2.62) in FTC versus FTA. FIGS. 4A and 4B show that most of the more abundant proteins in the FTC tumors are involved in cytoskeletal structure and cell organization, whereas nearly half of the proteins underabundant in FTC function in protein synthesis and folding. For some of the proteins (e.g., HSP gp96, PDI A3, cytokeratin 8, and β-actin), several distinct isoforms were shown to change in the same direction. In three cases (cytokeratin 8, β-actin, and histone H2B), some isoforms showed a lower abundance in the FTC sample, whereas other isoforms showed a higher abundance in the FTC compared with the FTA samples (Tables 1A-2B, FIGS. 1A-2B, respectively).

Immunohistochemistry

Figure 5:
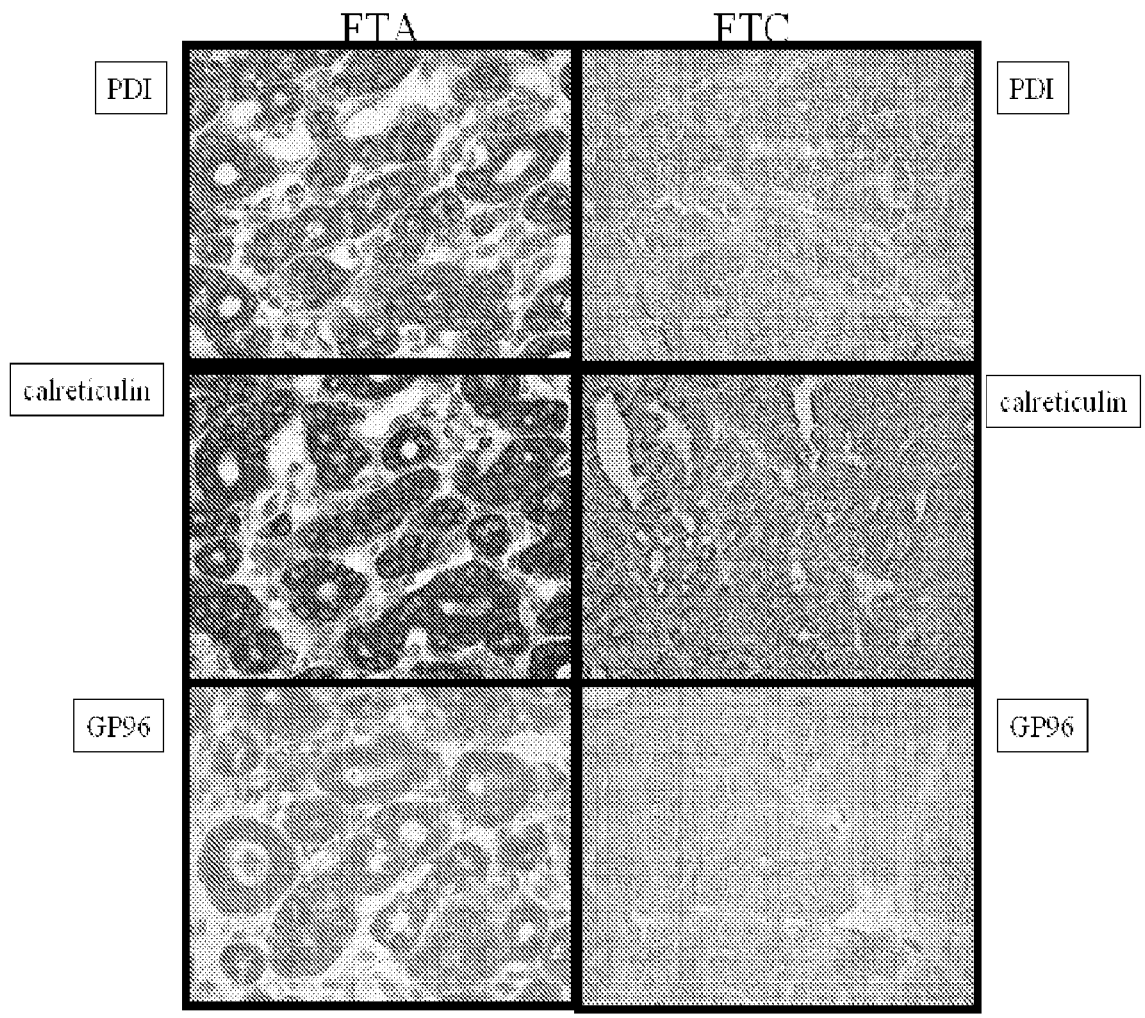
FIG. 5 is immunohistochemical analysis (Magnification=40×) showing lower intensity staining for PDI A3 (PDI), calreticulin, and HSP gp96 in FTC relative to FTA in the paraffin-embedded tissue samples.

Immunohistochemical validation studies were performed on independent paraffin-embedded tissue samples from patients with benign and malignant follicular thyroid tumors using antibodies against three of the identified proteins: HSP gp96, calreticulin, and PDI A3. These proteins were chosen based on their abundance, large volume ratio difference, absence of prior studies reporting their association with follicular thyroid neoplasia, and the availability of commercial antibodies. FIG. 5 shows the immunostaining of HSP gp96, calreticulin, and PDI A3 on 18 FTA and 16 FTC tissue samples. The staining intensity scores for the individual samples are presented in Tables 3A and 3B (FIGS. 6A and 6B, respectively).

All three putative markers were under abundant in FTC based on DIGE analysis. An optimal marker (or combination of markers) identify most or all malignancies (high sensitivity/negative predictive value), especially all widely invasive carcinomas, while minimizing the number of "benign" follicular adenomas subjected to surgery (high specificity/positive predictive value). Sensitivity analysis for these markers is shown in Table 4 (FIG. 7). Calreticulin (staining $\leq 3+$) had a high negative predictive value, whereas combining the three markers (any marker $\leq 2+$) had an excellent positive predictive value while still retaining a fairly high negative predictive value.

Protein Biomarkers of Follicular Thyroid Carcinoma

Figure 8:
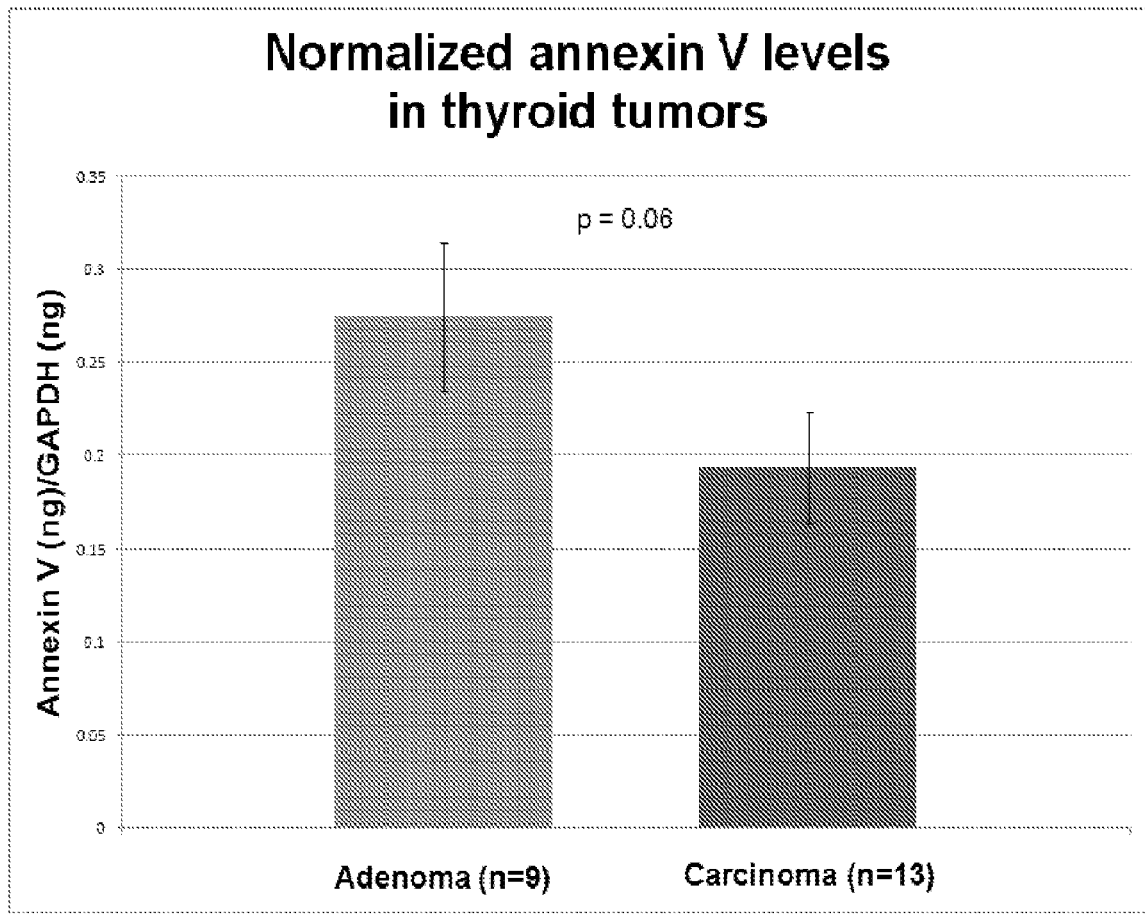
FIG. 8 shows the normalized measures of annexin V in 22 thyroid tumors.

Annexin V levels in human thyroid tumor whole cell lysates were measured by enzyme linked immunosorbent assay (Annexin V BioAssay™ ELISA Kit; US Biological, Swampscott, Mass.). These values were normalized to levels of glyceraldehydes-3-phosphate dehydrogenase (GAPDH) in the same lysates as determined by ELISA (GAPDH ELISA Test Kit; Bioo Scientific, Austin, Tex.). In the gel-based discovery studies GAPDH was detected and levels were unchanged between adenomas and carcinomas, validating its use as a normalization factor. FIG. 8 shows the normalized measures of annexin V in 22 thyroid tumors. The error bars represent the standard error of the measurements in each group and the p-value was determined using a t-test. It is believed that the sensitivity and specificity of biomarkers of thyroid carcinoma disclosed herein including annexin V will increase as the number of data (e.g, tumors study) increase.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A method for determining whether a thyroid nodule in a subject is a follicular thyroid adenoma (FTA) or a follicular thyroid carcinoma (FTC), said method comprising:
   determining the abundance of a marker protein in a sample obtained from the subject, wherein the sample comprises a thyroid nodule, a tissue, a fluid sample, or a combination thereof, and wherein the marker protein comprises hexokinase-1, glucosidase 2 beta subunit, aminoacylase-1, HSP 90-beta, cytosolic nonspecific dipeptidase, p100 co-activator, and 26S proteasome non-ATPase regulatory subunit 13; and comparing the abundance of the marker protein to a reference level of the marker protein to determine whether the thyroid nodule in the subject is FTA or FTC.

2. The method of claim 1, wherein said method further comprises:
determining abundance of a second marker protein comprising 14-3-3 protein gamma, pyridoxine-5'-phosphate oxidase, nucleoside-diphosphate kinase 1 isoform b, and dodecenoyl-CoA isomerase; and
comparing the abundance of the second marker protein to a reference level of the second marker protein to determine whether the thyroid nodule in the subject is FTA or FTC.

3. The method of claim 1, wherein the reference marker protein level is obtained from a normal subject, and wherein under abundance of the marker protein in the sample obtained from the subject compared to the reference level of the marker protein is an indication that the thyroid nodule in the subject is FTC.

4. The method of claim 1, wherein the reference level of the marker proteins comprises the marker protein level in a subject having follicular thyroid adenoma (FTA).

5. The method of claim 1, wherein the reference level of the marker proteins comprises the marker protein level in a subject having a follicular thyroid carcinoma (FTC).

6. A method for determining whether a follicular-derived thyroid neoplasm in a subject is malignant or benign, said method comprising:
determining a level of a marker protein in a sample obtained from the subject, wherein the sample comprises a thyroid nodule, a tissue, a fluid sample, or a combination thereof, and wherein the marker protein comprises hexokinase-1, glucosidase 2 beta subunit, aminoacylase-1, HSP 90-beta, cytosolic nonspecific dipeptidase, p100 co-activator, and 26S proteasome non-ATPase regulatory subunit 13, and
comparing the determined marker protein level to a reference level of the marker protein to determine whether the follicular-derived thyroid neoplasm in the subject is malignant or benign.

7. The method of claim 6 further comprising:
determining abundance of a second marker protein comprising 14-3-3 protein gamma, pyridoxine-5'-phosphate oxidase, nucleoside-diphosphate kinase 1 isoform b, and dodecenoyl-CoA isomerase; and
comparing the abundance of the second marker protein to a reference level of the second marker protein to determine whether the follicular-derived thyroid neoplasm in the subject is malignant or benign.

8. The method of claim 6, wherein the reference level of marker protein comprises the marker protein level in a subject having follicular thyroid adenoma (FTA).

9. The method of claim 6, wherein the reference level of marker protein comprises the marker protein level in a subject having follicular thyroid carcinoma (FTC).

10. The method of claim 7, wherein under abundance of the marker protein, over abundance of the second marker protein, or a combination thereof is an indication that the follicular-derived thyroid neoplasm is malignant.

11. The method of claim 6, wherein the abundance of the marker protein is determined using an analytical method comprising enzyme-linked immunosorbent assay (ELISA), immunoblot, immunohistochemistry, mass spectrometry or a combination thereof.

12. The method of claim 6, wherein the reference marker protein level is obtained from a normal subject, and wherein under abundance of the marker protein in the sample obtained from the subject compared to the reference level of the marker protein is an indication that the thyroid nodule in the subject is malignant.

* * * * *